United States Patent
Van Engeland et al.

(10) Patent No.: US 11,078,544 B2
(45) Date of Patent: *Aug. 3, 2021

(54) METHOD FOR IDENTIFYING SUBJECTS WITH AGGRESSIVE MELANOMA SKIN CANCER AT DIAGNOSIS

(71) Applicants: UNIVERSITEIT MAASTRICHT, Maastricht (NL); ACADEMISCH ZIEKENHUIS MAASTRICHT, Maastricht (NL)

(72) Inventors: Manon Van Engeland, Susteren (NL); Leander Pieter Jo Van Neste, Hoegaarden (BE); Karin Van Den Hurk, Hillegom (NL)

(73) Assignees: Universiteit Maastricht, Maastricht (NL); Academisch Ziekenhuis Maastricht, Maastricht (NL)

( * ) Notice: Subject to any disclaimer, the term of this patent is extended or adjusted under 35 U.S.C. 154(b) by 200 days.

This patent is subject to a terminal disclaimer.

(21) Appl. No.: 16/289,897

(22) Filed: Mar. 1, 2019

(65) Prior Publication Data

US 2019/0256926 A1 Aug. 22, 2019

Related U.S. Application Data

(63) Continuation of application No. 15/577,185, filed as application No. PCT/EP2016/061913 on May 26, 2016, now Pat. No. 10,260,109.

(30) Foreign Application Priority Data

May 29, 2015 (EP) .................................... 15169951

(51) Int. Cl.
*C12Q 1/68* (2018.01)
*C12Q 1/6886* (2018.01)

(52) U.S. Cl.
CPC ...... *C12Q 1/6886* (2013.01); *C12Q 2600/112* (2013.01); *C12Q 2600/118* (2013.01); *C12Q 2600/154* (2013.01)

(58) Field of Classification Search
None
See application file for complete search history.

(56) References Cited

FOREIGN PATENT DOCUMENTS

| WO | 2012037128 A2 | 3/2012 |
| WO | 2013135830 A1 | 9/2013 |
| WO | 2014072700 A1 | 5/2014 |
| WO | WO-2014072700 A1 * | 5/2014 ......... C07K 16/2851 |
| WO | 2015052537 A1 | 4/2015 |
| WO | 2016193117 A1 | 12/2016 |

OTHER PUBLICATIONS

Gao et al. (2013 Pigment Cell Melanoma Res 26: 542-554) (Year: 2013).*
Haas et al. (EMBO Mol Med (2013) 5, 413-429) (Year: 2013).*
NCBI GEO2R data output for GSE45266 query for profile graph of cg 10107725 obtained from https://www.ncbi.nlm.nih.gov/geo/geo2r/?acc=GSE45266 on Jul. 20, 2018, 2 pages (Year: 2018).*
Wajed et al. (Annals of Surgery, 2001, vol. 234, No. 1, 10-20) (Year: 2001).*
Derks et al. (Cellular Oncology 26 (2004) 291-299). (Year: 2004).*
Abbas et al., Cutaneous Malignant Melanoma: Update on Diagnostic and Prognostic Biomarkers, Am J Dermatopathol, 2014, pp. 363-379, vol. 36.
De Araujo et al., DNA Methylation Levels of Melanoma Risk Genes Are Associated with Clinical Characteristics of Melanoma Patients, Biomed Research International, Jan. 1, 2015, pp. 1115-1118, vol. 94, No. 4.
NCBI GE02R data output for GSE45266 query for profile graph of cg 10107725 obtained from https://www.ncbi.nlm.nih.gov/geo/geo2r/acc=GSE45266 on Jul. 20, 2018, 2 pages (Year: 2018).
PCT International Search Report and Written Opinion, PCT/EP2016/061913, dated Jul. 22, 2016.

* cited by examiner

*Primary Examiner* — Juliet C Switzer
(74) *Attorney, Agent, or Firm* — Patent Law Works, LLP

(57) ABSTRACT

This disclosure is in the field of molecular biology and medical diagnosis and provides means and methods for determining the prognosis and disease outcome of a subject having a melanoma. More in particular, this disclosure provides a method for determining whether a subject having a melanoma has a poor prognosis, the method comprising the step of determining in a sample from the subject whether the LY75 promoter is methylated and if the LY75 promoter is methylated, classifying the subject as having a poor prognosis.

7 Claims, 5 Drawing Sheets

Specification includes a Sequence Listing.

METHOD FOR IDENTIFYING SUBJECTS WITH AGGRESSIVE MELANOMA SKIN CANCER AT DIAGNOSIS

CROSS-REFERENCE TO RELATED APPLICATIONS

This application is a continuation of U.S. patent application Ser. No. 15/577,185, filed Nov. 27, 2017, pending, which is a national phase entry under 35 U.S.C. § 371 of International Patent Application PCT/EP2016/061913, filed May 26, 2016, designating the United States of America and published in English as International Patent Publication WO 2016/193117 A1 on Dec. 8, 2016, which claims the benefit under Article 8 of the Patent Cooperation Treaty to European Patent Application Serial No. 15169951.9, filed May 29, 2015.

STATEMENT ACCORDING TO 37 C.F.R. § 1.821(c) or (e)—SEQUENCE LISTING SUBMITTED AS ASCII TEXT FILE

Pursuant to 37 C.F.R. § 1.821(c) or (e), a file containing an ASCII text version of the Sequence Listing has been submitted concomitant with this application, the contents of which are hereby incorporated by reference.

TECHNICAL FIELD

The disclosure is in the field of molecular biology and medical diagnosis. It provides means and methods for determining the prognosis and disease outcome of a subject having a melanoma.

BACKGROUND

Cutaneous melanoma is a lethal skin tumor with continuously rising incidence, resulting in a growing healthcare burden [1, 2]. Worldwide, roughly 232,000 new cases and 55,000 deaths were reported in 2012 [3]. Patients diagnosed with localized disease have a five-year survival rate of more than 95% after treatment by surgical excision alone [4]. If the cancer is more advanced, however, survival rates drop substantially, i.e., 30% to 60% after five years, primarily depending on the tumor thickness, i.e., Breslow's depth.

Metastatic disease generally leads to poor patient outcomes, as treatment options were limited for a long time. However, rapid development of next-generation sequencing technologies has identified most genetic alterations and molecular pathways involved in melanoma development and provided the basis for novel targeted therapies [5]. Moreover, novel immunomodulatory therapies are successfully being developed for melanoma treatment [6].

Currently, the American Joint Committee on Cancer (AJCC) classifies patients predominantly based on histological features of the primary tumor, i.e., Breslow thickness, ulceration, and mitotic rate, and indicates that the initial biopsy is a critical component of both diagnosis and staging [7]. In addition, the presence of advanced disease stage (stage III/IV) and, to a lesser extent, patient age, gender, and tumor location, are prognostic melanoma factors. Breslow thickness is viewed as the most important prognostic parameter, however, 20-30% of patients diagnosed with thin melanomas (≤2.0 mm thickness) still die from their disease [8, 9]. Hence, improvements to the current staging system that lead to more accurate prediction of prognosis are warranted, allowing clinicians to better address prognosis of individual patients. Moreover, it is of importance to identify high-risk patients with aggressive disease at an early stage as these patients may benefit from more extensive surgery, adjuvant therapy, and closer follow-up.

In summary, cutaneous melanoma is a highly aggressive skin cancer that accounts for approximately 75% of skin cancer-related deaths. Despite an increased understanding of the biology of melanoma development and the identification of molecular alterations that accompany melanoma progression [10, 30], the AJCC melanoma staging and classification system has not yet incorporated potential molecular changes [7]. However, improvements to the current staging system are necessary to more accurately identify individual patients with aggressive disease at diagnosis. These patients with a so-called poor prognosis might benefit from additional therapy leading to improved clinical management and better patient outcome.

BRIEF SUMMARY

It was found that methylation of the promoter of lymphocyte antigen 75 (LY75), also known as CD-205 or DEC-205, is a strong marker that predicts poor clinical outcome, independent of the currently used prognosticators in an independent melanoma series. The disclosure, therefore, relates to a method for determining whether a subject having a melanoma has a poor prognosis, the method comprising the step of determining in a sample from the subject whether the LY75 promoter is methylated and if the LY75 promoter is methylated, classifying the subject as having a poor prognosis.

BRIEF DESCRIPTION OF THE DRAWINGS

FIG. 1A: Kaplan-Meier curve of melanoma-specific survival of patients grouped according to primary tumor thickness divided by AJCC tumor stage. FIG. 1B: Kaplan-Meier curve of melanoma-specific survival of patients grouped according to the presence or absence of tumor ulceration. FIG. 1C: Kaplan-Meier curve of melanoma-specific survival of patients grouped according to localized disease (Stage I/II) and metastatic disease (Stage III/IV). FIG. 1D: Kaplan-Meier curve of melanoma-specific survival of patients grouped according to LY75 promoter methylation.

DETAILED DESCRIPTION

The methylation status of the lymphocyte antigen 75 (LY75) promoter was examined in a well-characterized series of 123 primary melanomas with follow-up data. It was found that LY75 promoter methylation (HR=4.442; 95%-CI 2.307-8.553, P<0.001), together with ulceration (HR=2.262; 95%-CI 1.164-4.396, P=0.016), and metastatic disease at diagnosis (HR=5.069; 95%-CI 2.489-10.325, P<0.001) were significant predictors of melanoma survival.

LY75, also known as CD-205 or DEC-205, is a collagen-binding mannose family receptor that is predominantly expressed on thymic cortical epithelium and myeloid dendritic cell subsets [37]. LY75 has been reported to play a role in the endocytic uptake of antigen leading to both CD4+ and CD8+ T-cell response [37-39].

LY75 is Ensemble gene ID ENSG00000054219, situated at chromosome 2, with gene description Lymphocyte antigen 75 Precursor (DEC-205) (gp200-MR6) (CD205 antigen).

LY75 gene promoter was analyzed for its methylation status in melanoma cell lines and normal human epidermal melanocytes (NHEM), and in 20 primary melanoma samples and 20 common nevus samples. It was found that the promoter was methylated in 6 out of 6 melanoma cell lines, not in the NHEM cells, in 35% of the pilot melanomas and in 0% of the pilot nevi samples.

LY75 promoter methylation was identified as a strong predictor of poor melanoma prognosis and identified patients with aggressive disease at diagnosis independent of current prognostic parameters. LY75 promoter methylation is, therefore, an important aid in the identification of patients who require more extensive surgery, adjuvant treatment, and closer follow-up, which then leads to improved clinical outcome.

The disclosure, therefore, relates to a method for determining whether a subject having a melanoma has a poor prognosis, the method comprising a step of determining in a sample from the subject whether the LY75 promoter is methylated and if the LY75 promoter is methylated, classifying the subject as having a poor prognosis.

Figure 1A:
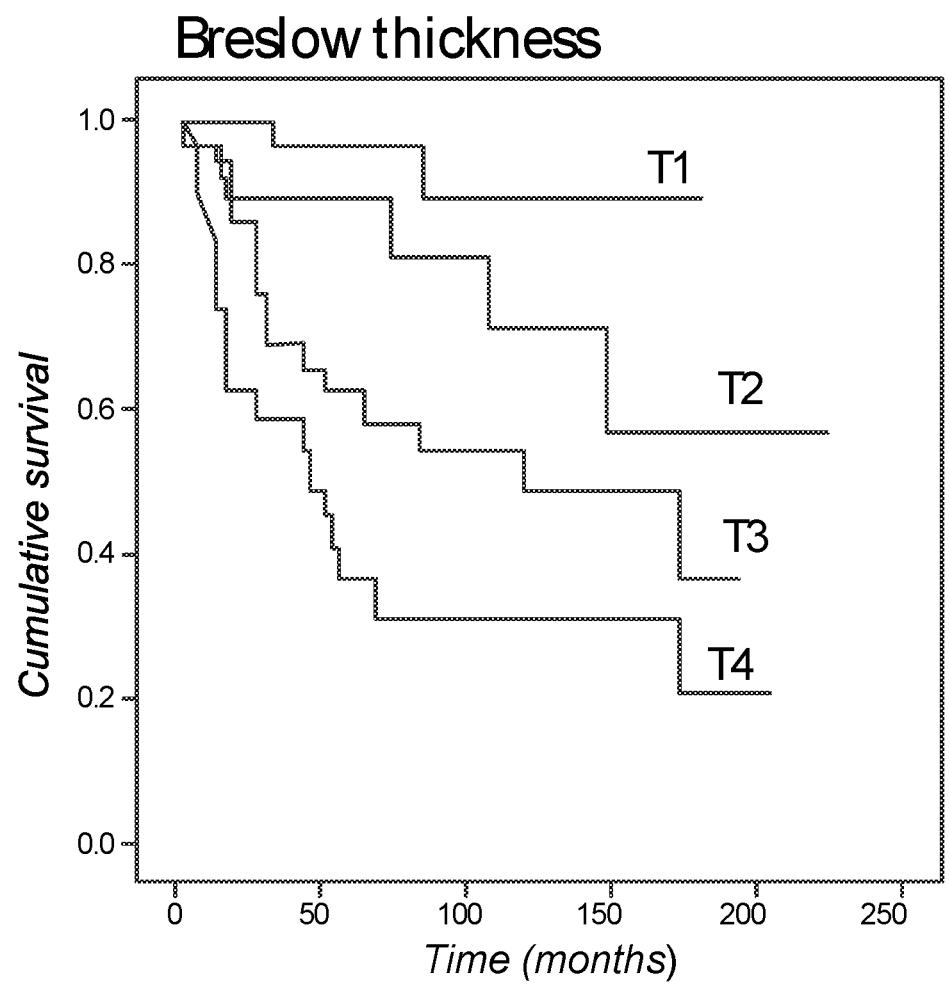
FIGS. 1A-1D: Kaplan-Meier survival curves of the best prognostic markers.
Figure 1B:
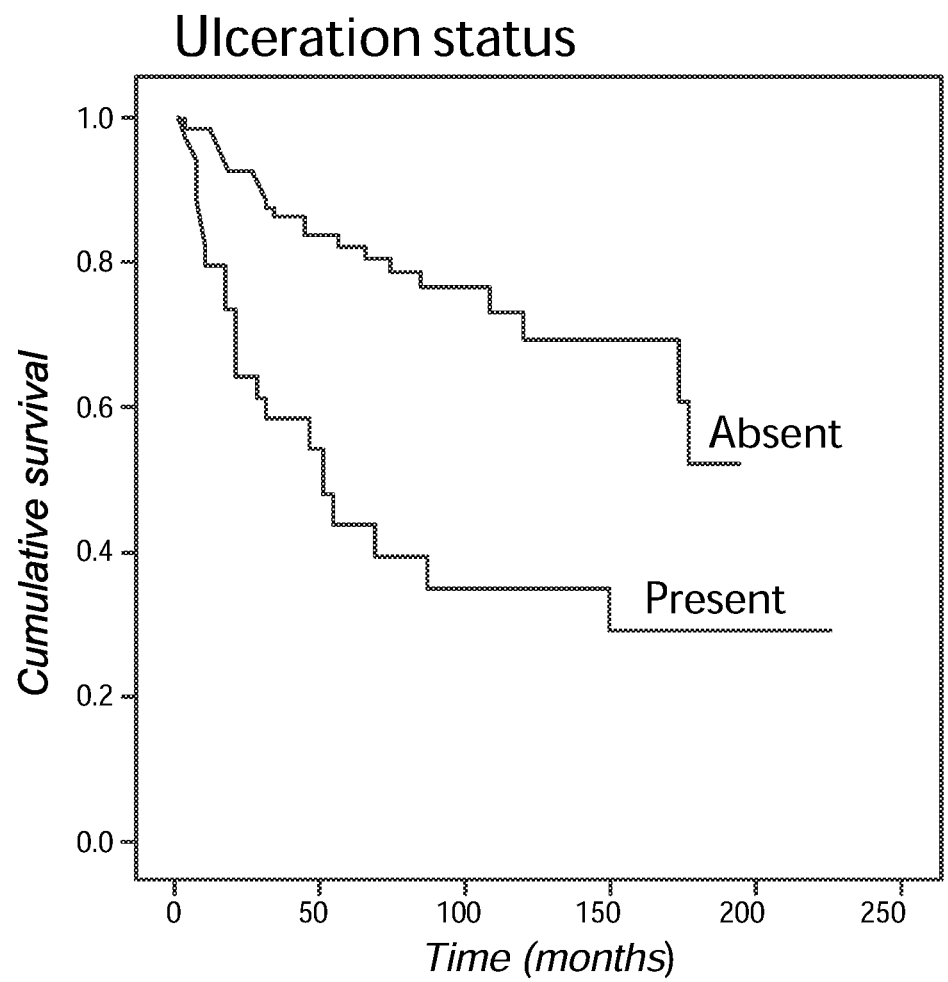
Figure 1C:
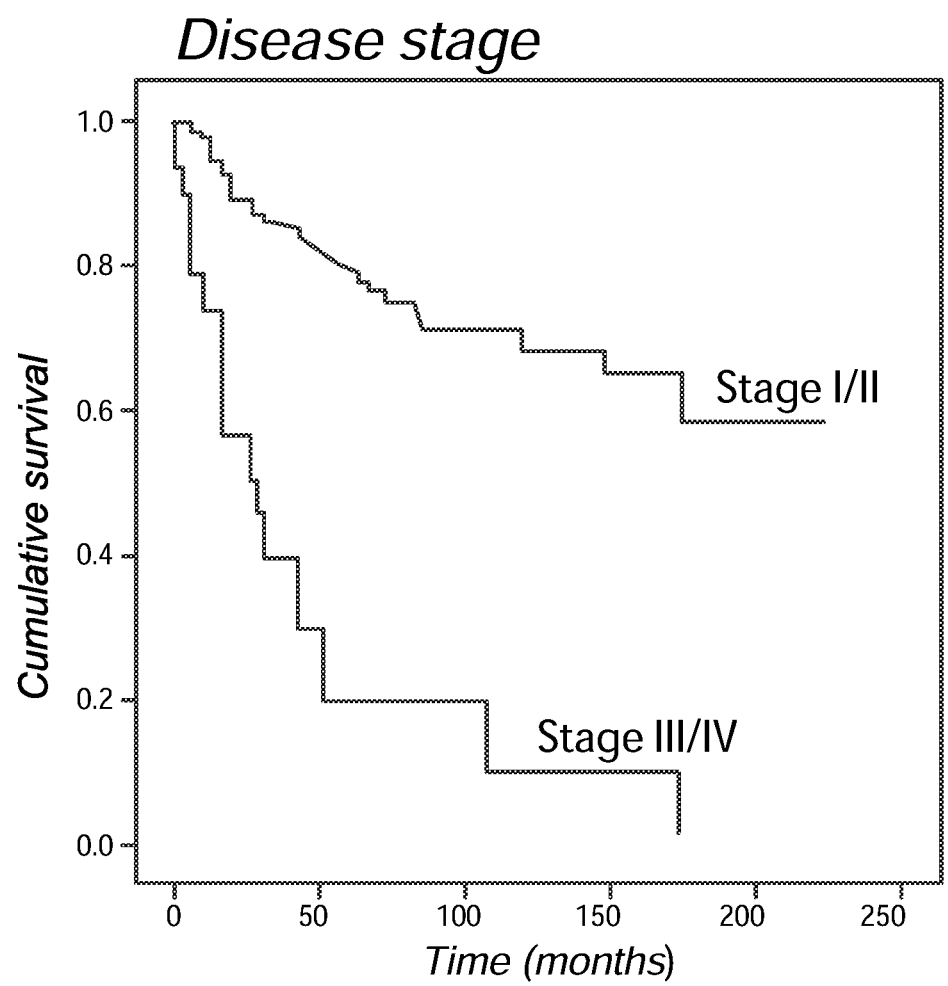
Figure 1D:
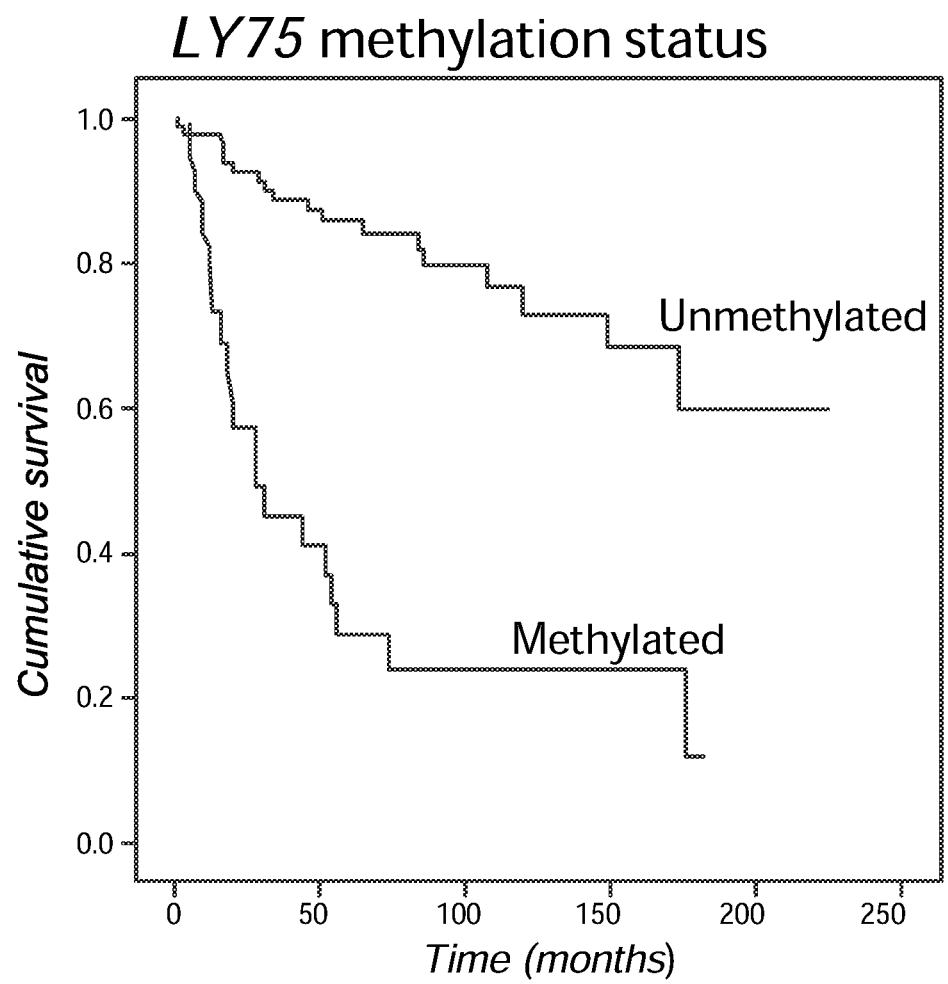
Figure 2:
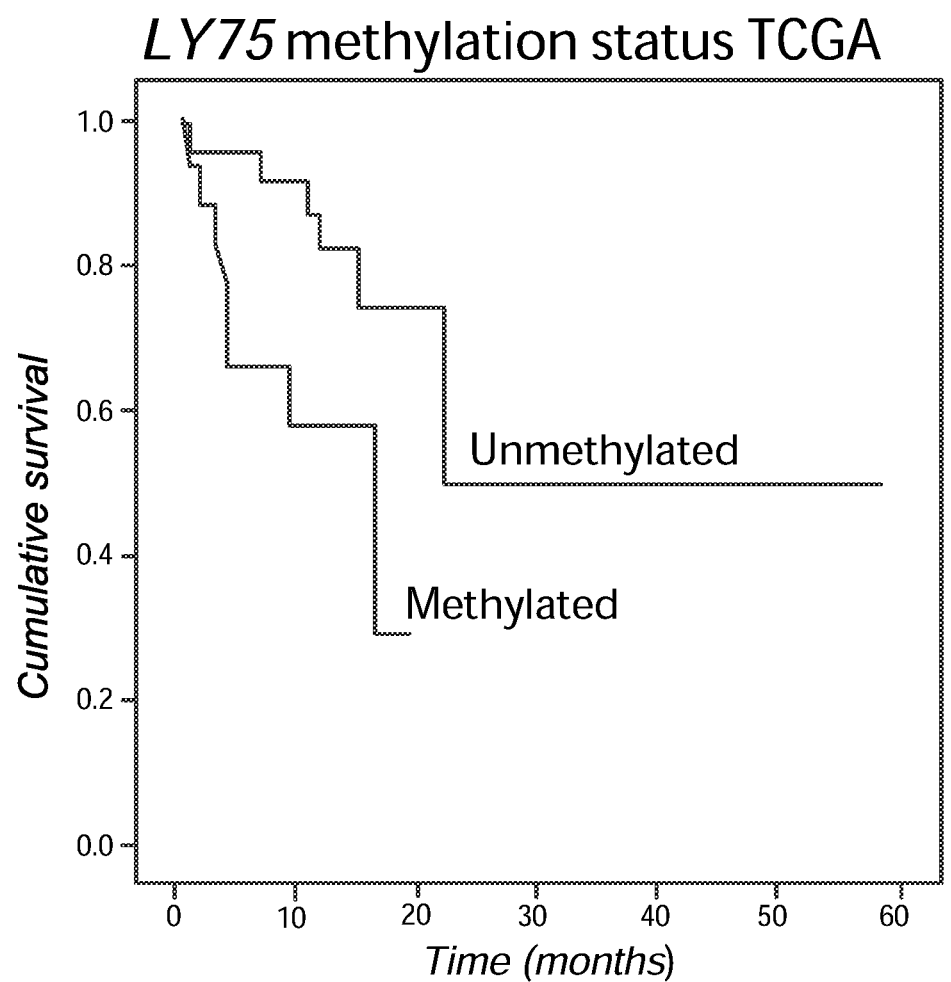
FIG. 2: Kaplan-Meier survival curve according to LY75 methylated promoter status. Kaplan-Meier survival curve of recurrence-free survival of TCGA patients grouped according to LY75 methylation status at probe cg24478096.

In the patient series examined herein, higher Breslow thickness, presence of ulceration, and presence of metastatic disease at diagnosis were the main prognostic indicators (P<0.001, Table 4; Kaplan-Meier survival curves depicted in FIGS. 1A, 1B, and 1C, respectively).

Additionally, a higher age at diagnosis, presence of tumor mitoses, and location on the head and neck were significant predictors of poor prognosis (Table 3), indicating that this series was suitable to study the additional prognostic value of methylation markers as it reflected the overall disease progression in a similar tendency as the general population.

The term "poor prognosis" is used herein to indicate that patients with a methylated LY75 promoter may be expected or be predicted to have a shorter life expectancy than those having an unmethylated LY75 promoter.

Tumor ulceration and metastatic disease at diagnosis were, together with LY75 methylation, the most significant predictors of survival. Using Akaike Information Criterion (AIC) showed that LY75 methylation as single methylation marker always outperformed this panel.

Since melanoma survival largely depends on the formation of lethal metastases, the question as to whether LY75 methylation was a significant predictor of distant metastases formation in disease stage I and II patients was researched. Of 95 stage I and II patients with known methylation status, a total of 26 patients developed metastatic disease. Using univariate analysis, a strong prognostic value of LY75 methylation to predict distant metastasis formation was observed, HR=7.835, 95%-CI 3.554-17.274, P<0.001. Applying multivariate analyses, promoter methylation of LY75 (HRLY75=7.924, 95%-CI 3.492-17.980, P<0.001) remained the best predictor of metastatic disease development together with ulceration (HRulceration=3.477, 95%-CI 1.579-7.655, P=0.002) and age (HRage=1.040, 95%-CI 1.009-1.072, P=0.011).

To validate the observed association of LY75 methylation with distant metastasis formation, the Cancer Genome Data Atlas (TCGA) dataset was evaluated. This dataset provides clinical follow-up data for 44 primary melanomas of which 14 patients did recur. (https://tcga-data.nci.nih.gov/tcga/)

For analysis, a single representative probe region was selected (cg24478096; wherein probe A: AAACAACAAAACTATAACATCAAAACACC-CAACAAACTACAAAAC TAACA (SEQ ID NO: 7), and probe B: AAACAACAAAACTATAACGTCGAAACACC CAACGAACTACGAAACTAACG (SEQ ID NO: 8) were employed. Probe A detects unmethylated alleles and probe B detects methylated alleles.

As a cut-off value, a normalized β-value of 0.2 was chosen, wherein B is equal to the intensities of the A and B probes according to the equation: B/(A+B). In other words, if the intensity of the B probe was more than 20% of the total intensity of probes A and B together, the sample was scored as having a methylated LY75 promoter. Samples with β-value >0.2 were thus scored as methylated and samples with β-value below or at 0.2 were scored as unmethylated.

It goes without saying that other cut-off values may be advantageously employed. Depending on the desired specificity and sensitivity of the method, the cut-off value may be adjusted.

TABLE 4

Associations of clinicopathological characteristics and methylation marker LY75 with melanoma-specific survival.

| | Univariate analysis | | | Multivariate analysis* | | | Final** | | |
|---|---|---|---|---|---|---|---|---|---|
| | HR | 95% CI | P-value | HR | 95% CI | P-value | HR | 95% CI | P-value |
| Current prognostic markers | | | | | | | | | |
| Gender (male vs female) | 1.675 | 0.900-3.116 | .103 | 1.612 | 0.810-3.206 | .174 | — | — | — |
| Age (continuous) | 1.026 | 1.004-1.050 | .023 | 1.007 | 0.982-1.032 | .595 | — | — | — |
| Location (head/neck vs other) | 2.875 | 1.451-5.697 | .002 | 2.206 | 1.018-4.780 | .045 | — | — | — |
| Breslow thickness (continuous) | 1.175 | 1.114-1.239 | <.001 | 1.154 | 1.073-1.242 | <.001 | — | — | — |
| Ulceration (yes vs no) | 3.355 | 1.827-6.160 | <.001 | 1.864 | 0.908-3.827 | .090 | 2.262 | 1.164-4.396 | .016 |
| Disease stage (stage III/IV vs stage I/II) | 6.498 | 3.372-12.520 | <.001 | 3.957 | 1.856-8.436 | <.001 | 5.069 | 2.489-10.325 | <.001 |
| Mitoses (>1 mm² vs <1 mm²)*** | 30.835 | 1.405-676.773 | .030 | — | — | — | — | — | — |
| Methylation marker; methylated vs unmethylated (% methylation) | | | | | | | | | |
| LY75    29/114(25%) | 5.395 | 2.854-10.200 | <.001 | 4.011 | 1.693-9.502 | .002 | 4.442 | 2.307-8.553 | <.001 |

*Multivariate Cox proportional hazards regression analyses were adjusted for gender, age, location, Breslow thickness, ulceration, and disease stage.
**Final analyses were the result of backward stepwise elimination on a saturated multivariate Cox proportional hazards regression model with the current prognostic makers (except for tumor mitoses) and methylation markers as covariates
***The wide 95% confidence interval for mitotic rate can be explained by the fact that none of the patients died of melanoma when mitoses were absent. As a result, the statistical analysis was problematic by the presence of a value equal to zero. Additionally, the AJCC staging system [7] uses the presence of mitoses only to categorize T1 melanoma (<1.0 mm thickness). For these reasons, tumor mitoses in multivariate analysis were left out.

The step of determining whether a subject has a methylated LY75 promoter may thus advantageously include a step of determining whether the level of methylation of the LY75 promoter is above a predetermined reference value or cut-off value. A skilled person may be well aware of ways of obtaining such a predetermined reference value. It may, for instance, be the value obtained using the same probes and methods as described herein when applied to a normal individual or a panel of normal individuals. It may also be an arbitrarily chosen value or it may be determined by trial and error. A preferred reference value is a beta value of more than 0.2 as determined with a suitable probe set, such as, for instance, probes A and B according to SEQ ID NO: 7 and SEQ ID NO: 8, respectively.

Kaplan-Meier survival analysis showed that primary melanomas that were methylated had a significantly higher risk to develop metastatic disease (log-rank P=0.020).

Backward stepwise elimination on a saturated multivariate Cox proportional hazards regression model with disease stage, Breslow thickness, tumor ulceration, gender, and age as covariates revealed that LY75 methylation was the best single marker to predict recurrence in this series ($HR_{LY75}$=3.568, 95%-CI 1.142-11.149, P=0.029).

Among stage I and II melanoma patients, LY75 methylation was the strongest predictor (HR=7.924, 95%-CI 3.492-17.980, P<0.001) of distant metastasis development, together with tumor ulceration (HR=3.477, 95%-CI 1.579-7.655, P=0.002) and older age at diagnosis (HR=1.040, 95%-CI 1.009-1.072, P=0.011). LY75 methylation outperformed Breslow thickness, the most important clinical prognostic parameter. This is especially of interest since the incidence of patients diagnosed with thin melanoma has been rising and an increasing proportion of melanoma-related deaths occur among these patients [8, 9, 36]. Thus, notwithstanding their generally favorable prognosis, thin melanomas contribute considerably (approximately 25%) to melanoma mortality. The identification of a strong relationship between LY75 methylation and poor prognosis that was irrespective of Breslow thickness provides a promising lead to identify high-risk patients, that are not detected by traditional risk factors, who might benefit from adjuvant therapy and closer follow-up.

Without wanting to be bound by theory, it was hypothesized that the poor clinical outcome of patients with LY75-methylated tumors might be partly explained by poor immune recognition, although a significant association of methylation with the absence of tumor-infiltrating lymphocytes (TILs) was not observed in the series (data not shown). However, it might also be that the TILs are functionally defective or incompletely activated as is commonly seen during tumor progression [40]. Melanoma is increasingly treated with immunomodulatory therapies, such as anti-CTLA4, and anti-PD1 antibodies that exploit the capacity of CD8+ T-cells to kill immunogenic melanoma cells [41, 42]. Although responses can be durable, the response rate to these therapies is generally low (roughly 25% of patients) [6] and biomarkers predicting response are thus far lacking [43]. It is, therefore, conceivable that LY75 methylation might reflect poor response to immune therapies as well.

In summary, LY75 methylation was recognized as a strong, independent predictor of poor prognosis, both in predicting melanoma-specific death and predicting the formation of distant metastases in stage I and II melanoma patients.

EXAMPLES

Example 1: Cell Culture and MBD-Sequencing

Methyl-binding domain (MBD)-sequencing was performed on six melanoma cell lines (WM35, WM3248, WM164, A375, M14, SK-MEL-28) and normal human epidermal melanocytes (NHEM) provided by Dr. Léon van Kempen (McGill University, Montreal, Canada). Authentication of all cell lines was performed using short tandem repeat (STR) profiling (DSMZ, Braunschweig, Germany). WM cell lines were cultured in W489 medium consisting of four parts of MCDB153 (Sigma-Aldrich, Zwijndrecht, The Netherlands) and one part of L15 (Sigma-Aldrich, Zwijndrecht, The Netherlands), A375, M14, and SK-MEL-28 cells were cultured in Dulbecco's modified Eagle's medium (Invitrogen, Breda, the Netherlands). Cells were supplemented with 2% or 10% heat inactivated fetal calf serum (Hyclone Perbio Science, Erembodegem-Aalst, Belgium), respectively. NREM cells were cultured in ready-to-use medium supplied by Promocell (Heidelberg, Germany). Genomic DNA was isolated using the PUREGENE® DNA isolation kit (Gentra systems, Minneapolis, Minn.) according to the manufacturer's instructions.

Genomic DNA of all samples was subjected to methylation-enrichment sequencing using the MethylCap kit with high-salt elution (Diagenode, Liege, Belgium) as described previously [25]. For each sample, and each methylation core, the maximum read count was used in downstream analyses.

Example 2: Total RNA Sequencing

RNA-sequencing on WM35, WM3248, M14, and SK-MEL-28 cells was performed to determine functional methylation, i.e., methylation associated with downregulated gene expression [26]. In brief, total ribonucleic acid (RNA) was isolated using the standard procedure for TRIzol® RNA extraction (Invitrogen, Bleiswijk, The Netherlands) and stored at −80° C. For total RNA sequencing, library preparation was carried out using a modified version of the Illumina "Directional mRNA-sequencing Sample Preparation" protocol with total RNA instead of mRNA. Ribosomal DNA was depleted from the DNA fraction using Illumina's Duplex-Specific Thermostable Nuclease normalization protocol for bidirectional mRNA sequencing (application note 15014673).

Example 3: Infinium-450K Data

Since The Cancer Genome Atlas (TCGA) has no methylation data available on control samples, Infinium-450K assays were performed on 14 fresh-frozen nevi, collected from the archives of the University Hospital of Leuven, Belgium, to be able to determine melanoma-specific methylation (Table 1).

TABLE 1

Samples used for methylation analysis

| Characteristics | No. of Patients | % |
|---|---|---|
| Common nevi used for Infinium-450K analyses (n = 14) | | |
| Gender | | |
| Female | 5 | 36 |
| Male | 9 | 64 |
| Age (years) | 20.6 ± 24. | |
| Location | | |
| Head and neck | 3 | 21 |
| Trunk | 8 | 57 |
| Extremities | 3 | 21 |

TABLE 1-continued

Samples used for methylation analysis

| Characteristics | No. of Patients | % |
|---|---|---|
| Common nevi used for validation with MSP (n = 20) | | |
| Gender | | |
| Female | 10 | 50 |
| Male | 10 | 50 |
| Age (years) | 31.7 ± 14.3 | |
| Location | | |
| Head and neck | 3 | 22 |
| Trunk | 11 | 57 |
| Extremities | 5 | 21 |

Genomic DNA from the 14 nevus samples was extracted as described previously [27]. DNA quantification was performed using a Qubit 2.0 plate reader (Invitrogen, Bleiswijk, The Netherlands) and PicoGreen dye (Invitrogen, Bleiswijk, The Netherlands). DNA quality was inspected on agarose gels stained with SYBR® Safe (Invitrogen, Bleiswijk, The Netherlands). Bisulfite conversion of DNA samples was carried out using the EZ DNA methylation kit (Zymo Research, Orange, Calif.) and converted DNA was hybridized on Infinium-450K BeadChips, following the Illumina Infinium HD Methylation protocol as described elsewhere [28].

Example 4: Patient Samples

LY75 Promoter CpG island methylation was examined in a well-characterized series of formalin-fixed, paraffin-embedded (FFPE) common nevi (n=20) and primary melanomas (n=123) of patients diagnosed at the Maastricht University Medical Centre, The Netherlands and University Hospital Leuven, Belgium. Collection, storage and use of all tissues and patient data were performed in agreement with the "Code for Proper Secondary Use of Human Tissue in the Netherlands." All of the used samples and corresponding data were de-linked and anonymized. Usage of both melanoma and healthy tissue samples was approved by the Maastricht Pathology Tissue Collection (MPTC) scientific committee. Detailed clinicopathological information of melanoma samples is shown in Table 2, characteristics of nevus samples are listed in Table 1.

TABLE 2

Clinicopathological characteristics of 123 primary melanoma cases with follow-up

| Characteristics | No. of Patients* | % |
|---|---|---|
| Gender | | |
| Female | 82 | 67 |
| Male | 41 | 33 |
| Age (years) | | |
| Mean | 59.9 ± 16.9 | |
| ≤50 years | 37 | 30 |
| >50 years | 86 | 70 |
| Disease stage | | |
| Localized - Stage I/II | 103 | 84 |
| Metastasized - Stage III/IV | 20 | 16 |
| Breslow thickness, mm | | |
| 0.01-1.0 | 32 | 26 |
| 1.01-2.0 | 29 | 24 |
| 2.01-4.0 | 29 | 24 |
| >4.0 | 33 | 27 |
| Ulceration | | |
| Absent | 86 | 70 |
| Present | 37 | 30 |
| Mitotic Rate | | |
| <1/mm$^2$ | 23 | 19 |
| ≥1/mm$^2$ | 99 | 81 |
| TILs | | |
| Absent | 29 | 24 |
| Non-brisk | 69 | 57 |
| Brisk | 24 | 20 |
| Histological subtype | | |
| SSM | 85 | 73 |
| NM | 21 | 18 |
| LMM | 9 | 8 |
| ALM | 2 | 2 |
| Location | | |
| Head and neck | 21 | 17 |
| Trunk | 33 | 28 |
| Extremities | 67 | 55 |
| Distant metastasis formation | | |
| No | 80 | 65 |
| Yes | 43 | 35 |
| Disease-related death | | |
| No | 81 | 66 |
| Yes | 42 | 34 |
| Mean follow-up (months) | 75.3 ± 57.0 | |

ALM, acral lentigious melanoma;
LMM, lentigo maligna melanoma;
NM, nodular melanoma;
SSM, superficial spreading melanoma;
TILs, tumor infiltrating lymphocytes Example 5: DNA Isolation, Bisulfite Conversion, and Promoter CpG Island Methylation Analyses A 4-µm section of each FFPE tissue block was stained with hematoxylin and eosin (H&E) and reviewed by an experienced dermato-pathologist. Cases that contained >50% nevus or melanoma cells were included. Subsequently, ten sections of 10 µm were cut and another H&E section was made to confirm the percentage of nevus and melanoma cells. Next, slides were deparaffinized and DNA was extracted following macro dissection with the QIA$_{AMP}$® DNA Micro Kit (Qiagen, Venlo, The Netherlands). NANODROP® quantification was used to estimate the quality and concentration of extracted DNA (NanoDrop ND-1000 Spectrophotometer). Sodium bisulphite modification of 500 ng genomic DNA was performed using the EPITECT® Bisulfite Kit (Qiagen, Venlo, The Netherlands) according to the manufacturer's instructions.

Following bisulfite conversion, nested, multiplex methylation-specific polymerase chain reaction (MSP) analyses were performed as described elsewhere [19]. Primer sequences and conditions are shown in Table 3. The number of PCR cycles performed was 30.

PCR conditions were as follows: The PCR mixture contains 1×PCR buffer (16.6 mM ammonium sulfate/67 mM Tris, pH 8.8/6.7 mM MgCl2/10 mM 2-mercaptoethanol), dNTPs (each at 1.25 mM), primers (300 ng each per reaction), and bisulfite-modified DNA ('50 ng) in a final volume of 50 ul. Reactions were hot-started at 95° C. for 5 minutes before the addition of 1.25 units of Taq polymerase (BRL). Amplification was carried out in a thermocycler for 30 cycles (30 seconds at 95° C., 30 seconds at the annealing temperature of 64° C., and 30 seconds at 72° C.), followed by a final 4-minute extension at 72° C. The flanking PCR was carried at 56° C. for 35 cycles.

PCR reactions were performed with controls for unmethylated alleles (for example, unmethylated human control DNA, EPITECT® Control DNA, Qiagen, Cat. no. 59568), methylated alleles (normal lymphocyte DNA treated in vitro with SssI methyltransferase [New England Biolabs]), and a no-template DNA control.

Ten μl of each MSP reaction was loaded onto 2% agarose gels containing GelStar Nucleic Acid Gel Stain (Cambrex, N.J., USA), and visualized under UV illumination. The presence of a PCR product performed with the methylated primers indicates the presence of methylated DNA and predicts a poor prognosis of the melanoma patient.

TABLE 3 primer sequences and conditions used for gene LY75:

| Direction | Position | Sequence | SEQ ID NO: | Temp (° C.) |
|---|---|---|---|---|
| Sense primer (5'->3') | Nested | TTAGGATGAGGATAGGTTGGG | 1 | 56 |
| | Unmethylated | GGATAGGTTGGGTGATTTTTTGTT | 2 | 64 |
| | Methylated | GGTTGGGCGATTTTTCGTC | 3 | 64 |
| Antisense primer (3'->5') | Nested | CAAACTAAAAACAACAAAACTATAAC | 4 | 56 |
| | Unmethylated | AAACTATAACATCAAAACACCCAACA | 5 | 64 |
| | Methylated | TATAACGTCGAAACACCCAACG | 6 | 64 |

Nested MSP reactions were performed with controls for unmethylated alleles (unmethylated human control DNA, EPITECT® Control DNA, Qiagen, Cat. no. 59568), methylated alleles (normal lymphocyte DNA treated in vitro with SssI methyltransferase [New England Biolabs]), and a no-template DNA control.

To ensure reproducibility, MSP reactions were performed in duplicate starting from DNA amplification with flanking primers. Discordant results were analyzed a third time, and the majority vote principle was used to determine the methylation status.

Example 6: Statistical Analyses

Cox proportional hazards regression was used to evaluate the effect of gene methylation and clinicopathological variables on melanoma-specific survival, resulting in hazard ratios (HRs) and their corresponding 95% confidence intervals (95%-CI). For LY75 methylation, the Cox proportional hazards model was used to evaluate the effect of methylation on distant metastasis formation (melanoma-free survival).

Survival time was defined as the time between first diagnosis and the first date of diagnosis of a distant metastasis. Akaike Information Criterion (AIC) was used to assess the predictive capacity of models with single and multiple methylation markers. The model with the lowest AIC was chosen as the best model. All reported P-values were two-sided, and P<0.05 was considered statistically significant. Analyses were performed using the statistical package IBM SPSS Statistics 21 (IBM, New York, USA) and R (R Foundation for Statistical Computing, Vienna, Austria).

REFERENCES

1. MacKie R M, Hauschild A, Eggermont A M. Epidemiology of invasive cutaneous melanoma. Ann Oncol, 2009. 20 Suppl 6: p. vi1-7.
2. Ferlay J, Shin H R, Bray F, et al. Estimates of worldwide burden of cancer in 2008: GLOBOCAN 2008. Int J Cancer, 2010. 127(12): p. 2893-2917.
3. Ferlay J, Soerjomataram I, Ervik M, Dikshit R, Eser S, Mathers C, Rebelo M, Parkin D M, Forman D, Bray, F. GLOBOCAN 2012 v1.0, Cancer Incidence and Mortality Worldwide: IARC CancerBase No. 11 [Internet]. Lyon, France: International Agency for Research on Cancer; 2013. Available from: http://globocan.iarc.fr, accessed on Jan. 9, 2014.
4. Gray-Schopfer V, Wellbrock C, Marais R. Melanoma biology and new targeted therapy. Nature, 2007. 445 (7130): p. 851-857.
5. Griewank K G, Scolyer R A, Thompson J F, et al. Genetic alterations and personalized medicine in melanoma: progress and future prospects. J Natl Cancer Inst, 2014. 106(2): p. djt435.
6. Miller D M, Flaherty K T, Tsao H. Current status and future directions of molecularly targeted therapies and immunotherapies for melanoma. Semin Cutan Med Surg, 2014. 33(2): p. 60-67.
7. Balch C M, Gershenwald J E, Soong S J, et al. Final version of 2009 AJCC melanoma staging and classification. J Clin Oncol, 2009. 27(36): p. 6199-6206.
8. Criscione V D, Weinstock M A. Melanoma thickness trends in the United States, 1988-2006. J Invest Dermatol, 2010. 130(3): p. 793-797.
9. Whiteman D C, Baade P D, Olsen C M. More People Die from Thin Melanomas (1 mm) than from Thick Melanomas (>4 mm) in Queensland, Australia. J Invest Dermatol, 2014. p.
10. van den Hurk K, Niessen H E, Veeck J, et al. Genetics and epigenetics of cutaneous malignant melanoma: a concert out of tune. Biochim Biophys Acta, 2012. 1826 (1): p. 89-102.
11. Laird P W. The power and the promise of DNA methylation markers. Nat Rev Cancer, 2003. 3(4): p. 253-266.
12. Heyn H, Esteller M. DNA methylation profiling in the clinic: applications and challenges. Nat Rev Genet, 2012. 13(10): p. 679-692.
13. Conway K, Edmiston S N, Khondker Z S, et al. DNA-methylation profiling distinguishes malignant melanomas from benign nevi. Pigment Cell Melanoma Res, 2011. 24(2): p. 352-360.
14. Sigalotti L, Covre A, Fratta E, et al. Whole genome methylation profiles as independent markers of survival in stage IIIC melanoma patients. J Transl Med, 2012. 10: p. 185.

15. Gao L, Smit M A, van den Oord J J, et al. Genome-wide promoter methylation analysis identifies epigenetic silencing of MAPK13 in primary cutaneous melanoma. Pigment Cell Melanoma Res, 2013. 26(4): p. 542-554.
16. Rakosy Z, Ecsedi S, Toth R, et al. Integrative genomics identifies gene signature associated with melanoma ulceration. PLoS One, 2013. 8(1): p. e54958.
17. Thomas N E, Slater N A, Edmiston S N, et al. DNA methylation profiles in primary cutaneous melanomas are associated with clinically significant pathologic features. Pigment Cell Melanoma Res, 2014. 27(6): p. 1097-1105.
18. Ecsedi S, Hernandez-Vargas H, Lima S C, et al. DNA methylation characteristics of primary melanomas with distinct biological behaviour. PLoS One, 2014. 9(5): p. e96612.
19. Gao L, van den Hurk K, Moerkerk P T, et al. Promoter CpG Island Hypermethylation in Dysplastic Nevus and Melanoma: CLDN11 as an Epigenetic Biomarker for Malignancy. J Invest Dermatol, 2014. p.
20. Carmona F J, Villanueva A, Vidal A, et al. Epigenetic disruption of cadherin-11 in human cancer metastasis. J Pathol, 2012. 228(2): p. 230-240.
21. Deng Z, Niu G, Cai L, et al. The prognostic significance of CD44V6, CDH11, and beta-catenin expression in patients with osteosarcoma. Biomed Res Int, 2013. 2013: p. 496193.
22. Li L, Ying J, Li H, et al. The human cadherin 11 is a pro-apoptotic tumor suppressor modulating cell stemness through Wnt/beta-catenin signaling and silenced in common carcinomas. Oncogene, 2012. 31(34): p. 3901-3912.
23. Song Y H, Shiota M, Kuroiwa K, et al. The important role of glycine N-methyltransferase in the carcinogenesis and progression of prostate cancer. Mod Pathol, 2011. 24(9): p. 1272-1280.
24. Huang Y C, Chen M, Shyr Y M, et al. Glycine N-methyltransferase is a favorable prognostic marker for human cholangiocarcinoma. J Gastroenterol Hepatol, 2008. 23(9): p. 1384-1389.
25. De Meyer T, Mampaey E, Vlemmix M, et al. Quality evaluation of methyl binding domain based kits for enrichment DNA-methylation sequencing. PLoS One, 2013. 8(3): p. e59068.
26. van Vlodrop I J, Niessen H E, Derks S, et al. Analysis of promoter CpG island hypermethylation in cancer: location, location, location! Clin Cancer Res, 2011. 17(13): p. 4225-4231.
27. van den Hurk K, Balint, B., Toomey S., O'Leary, P. C., Unwin, L., Sheahan, K., McDermott, E. W., Murphy, I., van den Oord, J. J., Rafferty, M., FitzGerald, D., Moran, J., Cummins, R., MacEneaney, O., Kay, E., O'Brien, C. P., Finn, S. P., Heffron, C. C. B. B., Murphy, M., Yela, R., Power, D. G., Regan, P. J., McDermott, C., O'Keeffe, A., Orosz, Z., Donnellan, P. P., Crown, J. P., Hennessy, B. T, and Gallagher, W. M. High-throughput oncogene mutation profiling reveals demographic differences in BRAF mutation rates among melanoma patients. Melanoma Research. Mel Res, 2015. In press: p.
28. Sandoval J, Heyn H, Moran S, et al. Validation of a DNA methylation microarray for 450,000 CpG sites in the human genome. Epigenetics, 2011. 6(6): p. 692-702.
29. Derks S, Lentjes M R, Hellebrekers D M, et al. Methylation-specific PCR unraveled. Cell Oncol, 2004. 26(5-6): p. 291-299.
30. Miller A J, Mihm M C, Jr. Melanoma. N Engl J Med, 2006. 355(1): p. 51-65.
31. Colabroy K L, Zhai H, Li T, et al. The mechanism of inactivation of 3-hydroxyanthranilate-3,4-dioxygenase by 4-chloro-3-hydroxyanthranilate. Biochemistry, 2005. 44(21): p. 7623-7631.
32. Mahapatra S, Klee E W, Young C Y, et al. Global methylation profiling for risk prediction of prostate cancer. Clin Cancer Res, 2012. 18(10): p. 2882-2895.
33. Litovkin K, Joniau S, Lerut E, et al. Methylation of PITX2, HOXD3, RASSF1 and TDRD1 predicts biochemical recurrence in high-risk prostate cancer. J Cancer Res Clin Oncol, 2014. 140(11): p. 1849-1861.
34. Huang Y W, Jansen R A, Fabbri E, et al. Identification of candidate epigenetic biomarkers for ovarian cancer detection. Oncol Rep, 2009. 22(4): p. 853-861.
35. Huang Y W, Luo J, Weng Y I, et al. Promoter hypermethylation of CIDEA, HAAO and RXFP3 associated with microsatellite instability in endometrial carcinomas. Gynecol Oncol, 2010. 117(2): p. 239-247.
36. Welch H G, Woloshin S, Schwartz L M. Skin biopsy rates and incidence of melanoma: population based ecological study. BMJ, 2005. 331(7515): p. 481.
37. Jiang W, Swiggard W J, Heufler C, et al. The receptor December-205 expressed by dendritic cells and thymic epithelial cells is involved in antigen processing. Nature, 1995. 375(6527): p. 151-155.
38. Bozzacco L, Trumpfheller C, Siegal F P, et al. December-205 receptor on dendritic cells mediates presentation of HIV gag protein to CD8+ T cells in a spectrum of human MHC I haplotypes. Proc Natl Acad Sci USA, 2007. 104(4): p. 1289-1294.
39. Cheong C, Choi J H, Vitale L, et al. Improved cellular and humoral immune responses in vivo following targeting of HIV Gag to dendritic cells within human antihuman DEC205 monoclonal antibody. Blood, 2010. 116 (19): p. 3828-3838.
40. Marincola F M, Jaffee E M, Hicklin D J, et al. Escape of human solid tumors from T-cell recognition: molecular mechanisms and functional significance. Adv Immunol, 2000. 74: p. 181-273.
41. Brahmer J R, Tykodi S S, Chow L Q, et al. Safety and activity of anti-PD-L1 antibody in patients with advanced cancer. N Engl J Med, 2012. 366(26): p. 2455-2465.
42. Hodi F S, O'Day S J, McDermott D F, et al. Improved survival with ipilimumab in patients with metastatic melanoma. N Engl J Med, 2010. 363(8): p. 711-723.
43. Griewank K G, Ugurel S, Schadendorf D, et al. New developments in biomarkers for melanoma. Curr Opin Oncol, 2013. 25(2): p. 145-151.
44. al-Tubuly A A, Luqmani Y A, Shousha S, et al. Differential expression of gp200-MR6 molecule in benign hyperplasia and down-regulation in invasive carcinoma of the breast. Br J Cancer, 1996. 74(7): p. 1005-1011.
45. Tungekar M F, Gatter K C, Ritter M A. Bladder carcinomas and normal urothelium universally express gp200-MR6, a molecule functionally associated with the interleukin 4 receptor (CD 124). Br J Cancer, 1996. 73(4): p. 429-432.
46. Al-Tubuly A A, Spijker R, Pignatelli M, et al. Inhibition of growth and enhancement of differentiation of colorectal carcinoma cell lines by MAb MR6 and IL-4. Int J Cancer, 1997. 71(4): p. 605-611.
47. Kaklamanis L, Koukourakis M I, Leek R, et al. Loss of interleukin 4 receptor-associated molecule gp200-MR6 in human breast cancer: prognostic significance. Br J Cancer, 1996. 74(10): p. 1627-1631.

48. Haas J, Frese K S, Park Y J, et al. Alterations in cardiac DNA methylation in human dilated cardiomyopathy. EMBO Mol Med, 2013. 5(3): p. 413-429.
49. Giridhar P V, Funk H M, Gallo C A, et al. Interleukin-6 receptor enhances early colonization of the murine omentum by upregulation of a mannose family receptor, LY75, in ovarian tumor cells. Clin Exp Metastasis, 2011. 28(8): p. 887-897.
50. Chapman E J, Kelly G, Knowles M A. Genes involved in differentiation, stem cell renewal, and tumorigenesis are modulated in telomerase-immortalized human urothelial cells. Mol Cancer Res, 2008. 6(7): p. 1154-1168.
51. Horn S, Figl A, Rachakonda P S, et al. TERT promoter mutations in familial and sporadic melanoma. Science, 2013. 339(6122): p. 959-961.
52. Huang F W, Hodis E, Xu M J, et al. Highly recurrent TERT promoter mutations in human melanoma. Science, 2013. 339(6122): p. 957-959.
53. Griewank K G, Murali R, Puig-Butille J A, et al. TERT promoter mutation status as an independent prognostic factor in cutaneous melanoma. J Natl Cancer Inst, 2014. 106(9): p.
54. Ioannidis J P. Biomarker failures. Clin Chem, 2013. 59(1): p. 202-204.

What is claimed is:

1. A method for treating a subject having melanoma with adjuvant therapy, the method comprising:
   determining in a sample from the subject that the LY75 promoter is methylated; and then treating the subject with adjuvant therapy so as to treat the melanoma.

2. The method according to claim 1, wherein the sample is obtained from the skin of the subject or from a melanoma.

3. The method according to claim 1, wherein the sample is obtained from a biopsy taken from the subject.

4. The method according to claim 1, further comprising determining tumor ulceration, determining metastatic disease at diagnosis, determining disease stage, and or determining Breslow thickness of the melanoma.

5. The method according claim 1, wherein the methylation status of the LY75 promoter is determined by polymerase chain reaction-based methylation analysis.

6. The method according to claim 5 wherein the polymerase chain reaction-based methylation analysis comprises nested primers.

7. The method according to claim 1, wherein 20% or more of the LY75 promoters in the sample are methylated.

* * * * *

SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Probes and primers for detection of methylated
      LY75 promoter

<400> SEQUENCE: 1
ttaggatgag gataggttgg g                                                 21

<210> SEQ ID NO 2
<211> LENGTH: 24
<212> TYPE: DNA
<213> ORGANISM: artificial sequence
<220> FEATURE:
<223> OTHER INFORMATION: Probes and primers for detection of methylated
      LY75 promoter

<400> SEQUENCE: 2
ggataggttg ggtgattttt tgtt                                              24

<210> SEQ ID NO 3
<211> LENGTH: 19
<212> TYPE: DNA
<213> ORGANISM: artificial sequence
<220> FEATURE:
<223> OTHER INFORMATION: Probes and primers for detection of methylated
      LY75 promoter

<400> SEQUENCE: 3
ggttgggcga ttttttcgtc                                                   19

<210> SEQ ID NO 4
<211> LENGTH: 27
<212> TYPE: DNA
<213> ORGANISM: artificial sequence
<220> FEATURE:
<223> OTHER INFORMATION: Probes and primers for detection of methylated
      LY75 promoter

<400> SEQUENCE: 4
caaactaaaa aacaacaaaa ctataac                                           27

<210> SEQ ID NO 5
<211> LENGTH: 26
<212> TYPE: DNA
<213> ORGANISM: artificial sequence
<220> FEATURE:
<223> OTHER INFORMATION: Probes and primers for detection of methylated
      LY75 promoter

```
<400> SEQUENCE: 5
aaactataac atcaaaacac ccaaca                                          26

<210> SEQ ID NO 6
<211> LENGTH: 22
<212> TYPE: DNA
<213> ORGANISM: artificial sequence
<220> FEATURE:
<223> OTHER INFORMATION: Probes and primers for detection of methylated
      LY75 promoter

<400> SEQUENCE: 6
tataacgtcg aaacacccaa cg                                              22

<210> SEQ ID NO 7
<211> LENGTH: 50
<212> TYPE: DNA
<213> ORGANISM: artificial sequence
<220> FEATURE:
<223> OTHER INFORMATION: Probes and primers for detection of methylated
      LY75 promoter

<400> SEQUENCE: 7
aaacaacaaa actataacat caaaacaccc aacaaactac aaaactaaca                50

<210> SEQ ID NO 8
<211> LENGTH: 50
<212> TYPE: DNA
<213> ORGANISM: artificial sequence
<220> FEATURE:
<223> OTHER INFORMATION: Probes and primers for detection of methylated
      LY75 promoter

<400> SEQUENCE: 8
aaacaacaaa actataacgt cgaaacaccc aacgaactac gaaactaacg                50
```